United States Patent [19]
Dillon et al.

[11] Patent Number: 5,891,021
[45] Date of Patent: Apr. 6, 1999

[54] PARTIALLY RIGID-PARTIALLY FLEXIBLE ELECTRO-OPTICAL SENSOR FOR FINGERTIP TRANSILLUMINATION

[75] Inventors: Andrew Joseph Dillon, Austin; Jeffrey Albert Secunda, Dallas; Todd Johnson, Frisco, all of Tex.

[73] Assignee: Perdue Holdings, Inc., Dallas, Tex.

[21] Appl. No.: 89,523

[22] Filed: Jun. 3, 1998

[51] Int. Cl.⁶ ................................................. A61B 5/00
[52] U.S. Cl. ............................................ 600/310; 600/344
[58] Field of Search ................................ 600/310, 322, 600/323, 340, 344, 473, 476

[56] References Cited

U.S. PATENT DOCUMENTS

| | | | |
|---|---|---|---|
| 3,167,658 | 1/1965 | Richter | 250/239 |
| 3,599,629 | 8/1971 | Gordy | 128/2.06 |
| 3,602,213 | 8/1971 | Howell et al. | 128/2.05 |
| 3,769,974 | 11/1973 | Smart et al. | 128/2.05 |
| 3,807,388 | 4/1974 | Orr et al. | 128/205 |
| 4,013,067 | 3/1977 | Kresse et al. | 128/2.05 |
| 4,091,803 | 5/1978 | Pinder | 128/2.05 |
| 4,305,401 | 12/1981 | Reissmueller et al. | 128/690 |
| 4,350,165 | 9/1982 | Striese | 128/640 |
| 4,370,984 | 2/1983 | Cartmell | 128/640 |
| 4,380,240 | 4/1983 | Jobsis et al. | 128/633 |
| 4,406,289 | 9/1983 | Wesseling et al. | 128/670 |
| 4,685,464 | 8/1987 | Goldberger et al. | 128/633 |
| 4,830,014 | 5/1989 | Goodman et al. | |
| 4,865,038 | 9/1989 | Rich et al. | 128/633 |
| 5,217,012 | 6/1993 | Young et al. | 128/633 |
| 5,249,576 | 10/1993 | Goldberger et al | 128/632 |
| 5,387,122 | 2/1995 | Goldberger et al. | 439/353 |
| 5,429,129 | 7/1995 | Lovejoy et al. | 128/633 |
| 5,676,139 | 10/1997 | Goldberger et al. | 128/633 |

*Primary Examiner*—Cary E. O'Connor
*Assistant Examiner*—Eric F. Winakur
*Attorney, Agent, or Firm*—Andrew J. Dillon

[57] ABSTRACT

A sensor is provided for transillumination of a blood-profused portion of a human fingertip. The sensor includes an opaque, semi-cylindrical substantially rigid cradle member having a photosensor mounted to a concave surface thereof such that ambient light cannot penetrate the cradle member and induce erroneous readings. A flexible planar web-like support structure is attached at one end thereof to the cradle member and includes a light source mounted within the web thereof. A repositionable adhesive coating on the concave surface of the cradle member holds the fleshy portion of a human fingertip in conformance therewith, and when the flexible planar web-like support structure is wrapped around a fingertip within the cradle member, the light source overlies the photosensor for transillumination of the fingertip.

18 Claims, 2 Drawing Sheets

PARTIALLY RIGID-PARTIALLY FLEXIBLE ELECTRO-OPTICAL SENSOR FOR FINGERTIP TRANSILLUMINATION

BACKGROUND OF THE INVENTION

1. Technical Field

This invention relates, in general, to improved electro-optical sensors for measurement of arterial oxygen saturation and, in particular, to electro-optical sensors for measurement of arterial oxygen saturation which have cutaneous conformance. Still more particularly, the present invention relates to an electro-optical sensor for measurement of arterial oxygen saturation which is mounted within a partially rigid-partially flexible sensor body which diminishes ambient light artifact and sensor damage.

2. Description of the Related Art

Pulse oximetry involves the continuous, non-invasive monitoring of the oxygen saturation level in blood-profused tissue to provide an early indication of impending shock. An oximeter probe typically is secured to the patient and provides an electrical signal to an oximeter device. The oximeter device houses electronic circuitry for processing this electric signal and generating human-readable indicia of the patient's blood oxygen saturation level. Both disposable and non-disposable sensor probes for this purpose are widely utilized.

Non-disposable probes are typically designed utilizing a clamp design. This design includes one or more light-emitting diodes which are adjacent to one side of a fleshy human appendage, such as a finger. Light from the light-emitting diode is received by a photosensor which is placed on the opposing fleshy side of the appendage. Such devices generally consist of a small spring-loaded clip which attaches like a common clothespin to the tip of a finger or similar appendage. While this technique works quite well in many applications, this design suffers from selected defects. For example, inaccurate measurements may result because of so-called "motion artifact" which is created by differential motion between the sensor and the patient's finger, as well as changes in pressure within the tissue. Further, these clamp-type sensors may become removed inadvertently. Additionally, the spring-loaded pressure on fleshy tissue over a period of time will cause a reduction of blood flow to that tissue. Reduction of blood flow will cause a concomitant loss of pulse amplitude and, thus, a loss of the optical signal to be measured. To minimize this constricted effect of clamp-type attachments, the sensor must be adjusted or repositioned frequently, generally once or twice per hour. These drawbacks result in this type of clamp sensor being unacceptable for long-term, uninterrupted measurement.

Disposable sensor probes also are known in the prior art. U.S. Pat. No. 4,830,014 discloses a sensor probe which comprises a light source and photosensor mounted within the web of an elongated flexible strip. The flexible strip is then wrapped around the human fingertip such that the light source and sensor are positioned in directly overlying relationship. The low mass and aspect ratio of such sensor probes minimize the motion artifact present within larger clamp-type sensors, and the adhesive nature of the elongated strip causes the sensor and light source to conform to the fingertip skin, minimizing the distortion brought about by pressure on fleshy tissue.

While the sensor disclosed within U.S. Pat. No. 4,830,014 provides relief from several of the defects known to exist within non-disposable sensor probes, these so-called "bandaid" sensors include various defects as well.

For example, the mounting of a light-emitting diode and sensor in a flexible bandaid-like structure can result in damage to either of these sensitive electronic devices. Further, the porous, translucent nature of the bandaid-like strip mount can result in erroneous readings when the patient is present within an area having high-ambient light in that the ambient light may penetrate the bandaid-like structure and affect the reading at the light sensor.

The so-called "bandaid" sensor also suffers physical frailty in that the conductors which electrically couple the light source and light sensor to the oximeter device are merely woven into the fabric of the bandaid-like structure and, thus, are subject to deformation and fatigue over long periods of time. Finally, the bandaid sensor, which wraps around the tip of the human finger, requires that any patient having a fingernail of greater than nominal length must trim that fingernail in order for the light source and sensor to overlie one another through the fingernail and a fleshy portion of the fingertip.

In view of the above, it should be apparent that a need exists for a disposable electro-optical sensor which may be utilized to transilluminate a human fingertip which possesses small mass but which provides some rigidity for sensor and conductor mounting and protection and which minimizes erroneous readings brought about by high-ambient light.

SUMMARY OF THE INVENTION

It is one object of the present invention therefore to provide an improved electro-optical sensor.

It is another object of the present invention to provide an improved electro-optical sensor for non-invasive photoelectric measurement of arterial oxygen saturation.

It is yet another object of the present invention to provide an improved electro-optical sensor for transillumination of the human fingertip which conforms to the skin thereof while providing a rigid protected mounting surface for a light sensor, light-emitting diodes and electrical conductors.

The foregoing objects are achieved as is now described. A sensor is provided for transillumination of a blood-perfused portion of a human fingertip. The sensor includes an opaque, semi-cylindrical substantially rigid cradle member having a photosensor mounted to a concave surface thereof such that ambient light cannot penetrate the cradle member and induce erroneous readings. A flexible planar web-like support structure is attached at one end thereof to the cradle member and includes a light source mounted within the web thereof. A repositionable adhesive coating on the concave surface of the cradle member holds the fleshy portion of a human fingertip in conformance therewith, and when the flexible planar web-like support structure is wrapped around a fingertip within the cradle member, the light source overlies the photosensor for transillumination of the fingertip.

The above as well as additional objectives, features and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

DETAILED DESCRIPTION OF PREFERRED EMBODIMENT

Figure 1:
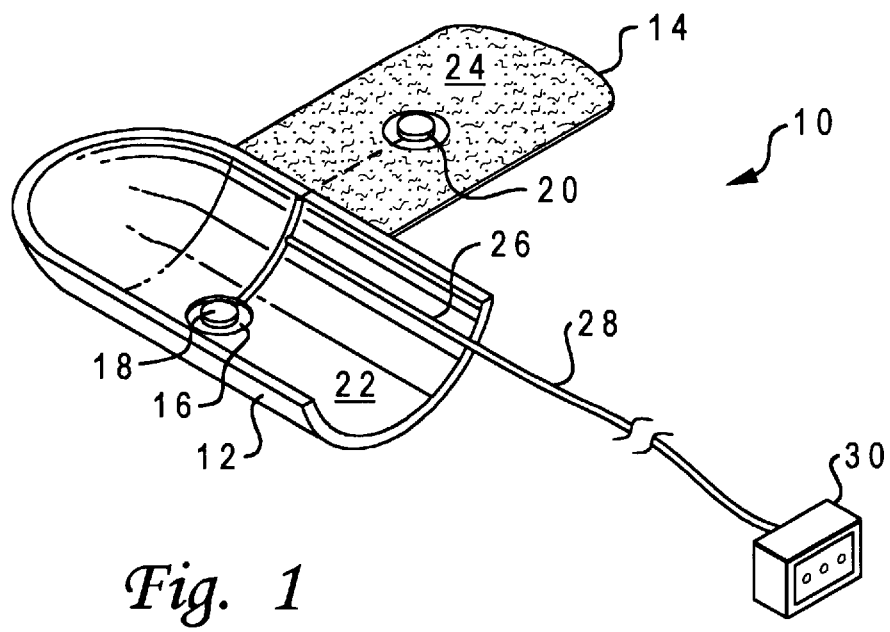
FIG. 1 is a perspective view of the electro-optical sensor of the present invention.

With reference now to the figures and, in particular, with reference to FIG. 1, there is depicted a perspective view of an electro-optical sensor 10 which may be utilized for transillumination of a blood-perfused portion of a human fingertip in order to measure light extinction during transillumination.

As illustrated, electro-optical sensor 10 is constructed of a partially rigid-partially flexible construction and includes an opaque, semicylindrical substantially rigid cradle member 12. Cradle member 12 is preferably constructed of molded plastic such as a polyolefin plastic and also may be constructed of polypropylene, polystyrene, polyethyline or any other suitable plastic material. In the embodiment depicted in FIG. 1, attached to the circumference of cradle member 12 is flexible, initially substantially web-like support structure 14. Support structure 14 may be constructed having an adhesive surface 24 which overlies an opaque vinyl strip. A porous, flexible tape layer having an adhesive side also may be utilized. Support structure 14 may be mounted to cradle member 12, utilizing adhesive, sonic welding or any other suitable technique.

As noted, cradle member 12 includes a concave surface 22 which, in accordance with one embodiment of the present invention, also may be coated with an adhesive in order to provide conformance with the skin of the fleshy portion of a human fingertip. As will be disclosed below, the adhesive surface 24 of support structure 14 and the adhesive coating on concave surface 22 of cradle member 12 may be provided utilizing a separate double-sided adhesive strip.

Still referring to concave surface 22 of cradle member 12, it may be seen that a recess 16 is provided therein. Recess 16 may be cut from concave surface 22 of cradle member 12 or molded into the surface thereof. Recess 16 communicates with electrical conductor channel 26 which, in a manner which will be explained in greater detail herein, may be utilized to position electrical conductors necessary to provide electrical power to various electronic components within electro-optical sensor 10.

As depicted within FIG. 1, electronic components 18 and 20 are mounted within electro-optical sensor 10. Electronic component 18 is preferably a photo-sensitive device which is mounted within recess 16, utilizing any suitable adhesive. In a similar manner, a pair of light-emitting diodes are mounted within electronic component 20, and fixedly mounted within an aperture within the web of support structure 14.

By mounting a photo-sensitive device 18 within recess 16 within concave surface 22 of cradle member 12, erroneous readings caused by ambient light may be minimized due to the opaque nature of cradle member 12; however, those having ordinary skill in the art will appreciate that, by manufacturing support structure 14 utilizing an opaque vinyl strip, the position of photo-sensitive device 18 and the light-emitting diodes depicted at reference numeral 20 may be reversed.

Electrical conductors from light-emitting diodes 20 and photo-sensitive device 18 are placed within electrical conductor channel 26 and extend from cradle member 12 at the open end thereof. In this manner, as those having ordinary skill in the art will appreciate, the electrical conductors may be protected from wear and fatigue which may occur as a result from mounting those conductors within a flexible vinyl strip as is known in the prior art. The electrical conductors are preferably sheathed within electrical cable 28 and electrically connected to adapter plug 30 which can be utilized to provide an electrical connection between electro-optical sensor 10 and a suitable oximeter device.

Figure 2:
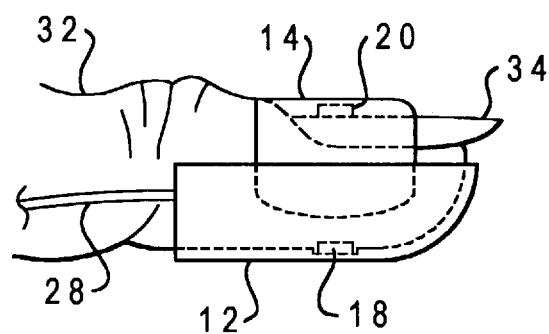
FIG. 2 is a side view of a human fingertip within the electro-optical sensor of FIG. 1.

Referring now to FIG. 2, there is depicted a side view of a human fingertip 32 within electro-optical sensor 10 of FIG. 1. As noted above, concave surface 22 of cradle member 12 is preferably coated with an adhesive such as any repositionable adhesive manufactured by 3M Corporation of St. Paul, Minn. Thereafter, human fingertip 32, when placed within cradle member 12, with the fleshy portion of fingertip 32 placed within cradle member 12, will cause substantial conformance between the skin of human fingertip 32 and concave surface 22 of cradle member 12. In this manner, photo-sensitive device 18 will be placed adjacent to the fleshy portion of fingertip 32. Thereafter, support structure 14 is wrapped around fingertip 32 such that light-emitting diodes 20 are disposed in an overlying relationship with photo-sensitive device 18. In one depicted embodiment of the present invention, support structure 14 includes an adhesive surface 24 which may be utilized to hold support structure 14 in a position wrapped around fingertip 32, around the circumference of cradle member 12.

The circumferential wrap of support structure 14 around cradle member 12 permits electro-optical sensor 10 to be utilized with patients having a long fingertip 34 which might otherwise preclude the use of a so-called "bandaid" disposable oximeter probe.

Figure 3:
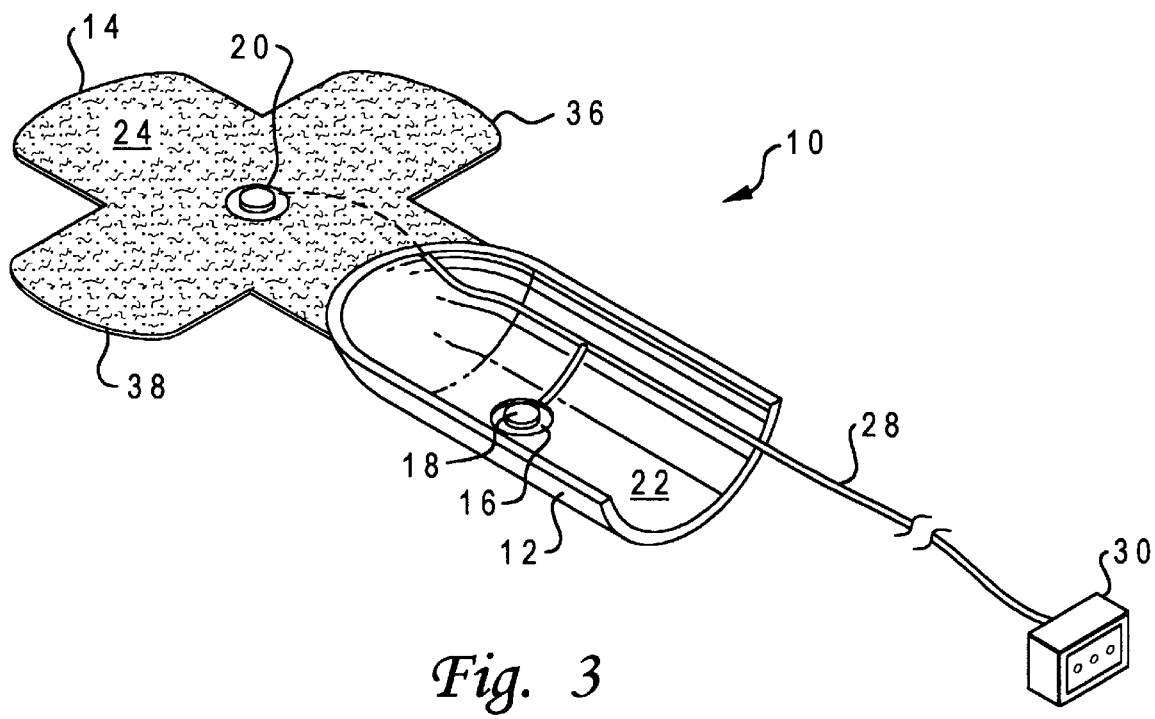
FIG. 3 is a perspective view of a second embodiment of the electro-optical sensor of the present invention.

With reference now to FIG. 3, there is depicted a perspective view of a second embodiment of electro-optical sensor 10. As depicted in this embodiment, support structure 14 is attached at the rounded end of cradle member 12.

All elements of the electro-optical sensor 10 of FIG. 3 which are identical to the electro-optical sensor 10 of FIG. 1 are labeled with like reference numerals. As depicted, photo-sensitive device 18 is mounted once again within recess 16 in concave surface 22 of cradle member 12. Light-emitting diodes 20 are mounted once again within the web of support structure 14. However, as depicted in FIG. 3, support structure 14 is mounted to the rounded end of cradle member 12 and thus may be wrapped around a fingertip in an axial fashion. Adhesive wings 36 and 38, as will be described below, may be utilized to hold support structure 14 in a fixed position wrapped around a human fingertip.

Figure 4:
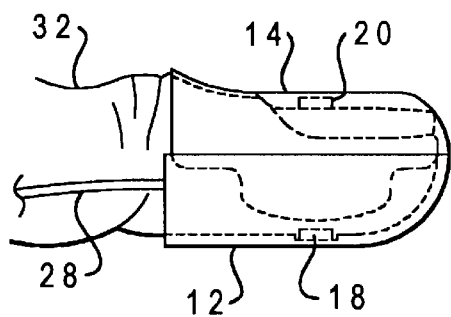
FIG. 4 is a side view of a human fingertip within the second embodiment of the electro-optical sensor of FIG. 3.

Referring now to FIG. 4, there is depicted a side view of a human fingertip 32 placed within electro-optical sensor 10 in the embodiment of FIG. 3. As illustrated, by wrapping support structure 14 in an axial fashion around human fingertip 32, which is placed within cradle member 12, light-emitting diodes 20 are placed once again in an overlying relationship with photo-sensitive device 18. Adhesive wings 36 and 38 may be utilized on the outer surface of cradle member 12 to hold support structure 14 in the position wrapped around fingertip 32.

Figure 5:
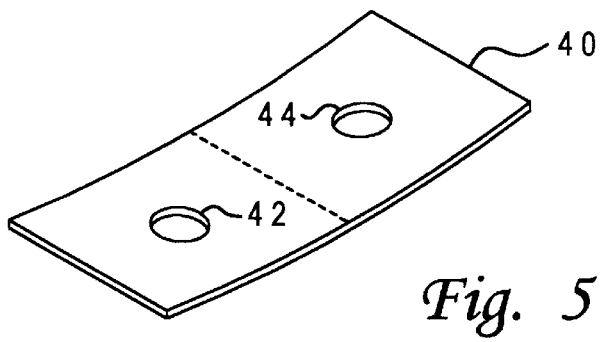
FIG. 5 is a perspective view of one embodiment of a repositionable adhesive layer which may be utilized with the electro-optical sensor of the present invention.

Finally, with reference to FIG. 5, there is depicted a perspective view of one embodiment of an adhesive layer which may be utilized with the electro-optical sensor of the present invention. As depicted, an adhesive layer 40 may be provided which includes apertures 42 and 44. In one preferred embodiment of the present invention, apertures 42 and 44 preferably directly overlie photo-sensitive device 18 and light-emitting diodes 20 in the embodiment depicted within FIG. 1. In an embodiment which utilizes the adhesive layer of FIG. 5, surface 24 of support structure 14 and concave surface 22 of cradle member 12 are manufactured without an adhesive layer. A double-sided adhesive layer 40, such as that depicted within FIG. 5, is applied to electro-optical sensor 10 such that apertures 42 and 44 overlie photo-sensitive device 18 and light-emitting diodes 20. The adhesive on one side of adhesive layer 40 retains adhesive layer 40 within electro-optical sensor, and the adhesive layer on the other side thereof may be utilized to ensure conformance between the skin of the human fingertip and electro-optical sensor 10.

Upon reference to the foregoing, those skilled in the art will appreciate that the electro-optical sensor depicted within the present application provides an enhanced physical mounting structure for sensitive electronic components while maintaining a low aspect ratio and mass so that motion artifact will be minimized. Further, the utilization of a rigid, opaque, semicylindrical cradle member diminishes substantially the likelihood of erroneous readings caused by the presence of ambient light. Further, the utilization of a circumferential wrap for the flexible support structure accommodates patients having fingernails which are longer than nominal length.

While the invention has been particularly shown and described with reference to a preferred embodiment, it will be understood by those skilled in the art that various changes in form and detail may be made therein without departing from the spirit and scope of the invention.

We claim:

1. A non-invasive electro-optical sensor for removable adhesive attachment to a fingertip of a patient for use in measuring light extinction during transillumination of the blood-perfused tissue within said fingertip, said sensor comprising:

an opaque, semi-cylindrical, substantially rigid cradle member having a concave surface, a convex surface and a diameter larger than the diameter of a human fingertip;

a flexible, initially substantially planar web-like support structure attached at one end thereof to said cradle member;

a photosensor mounted on said concave surface of said cradle member;

a light source mounted in said web like support structure, said light source having a light-emitting surface which directly overlies said photosensor when said support structure is wrapped around a human fingertip within said cradle member; and an adhesive layer on said concave surface of said cradle member for removably adhesively securing said concave surface of said cradle member to a fleshy portion of a human fingertip such that said concave surface is held in conformance with said human fingertip without stressing said human fingertip.

2. The non-invasive electro-optical sensor according to claim 1 further including means for securing said support structure in a wrapped position around a human fingertip within said cradle member such that said light source directly overlies said photosensor.

3. The non-invasive electro-optical sensor according to claim 1 wherein said opaque, semi-cylindrical, substantially rigid cradle member is constructed of molded polyolefin plastic.

4. The non-invasive electro-optical sensor according to claim 3 wherein said opaque, semi-cylindrical, substantially rigid cradle member is constructed of polypropylene.

5. The non-invasive electro-optical sensor according to claim 1 further including a recess within said concave surface of said cradle member for receiving said photosensor.

6. The non-invasive electro-optical sensor according to claim 1 further including an electrical conductor channel formed within said concave surface of said cradle member.

7. The non-invasive electro-optical sensor according to claim 1 wherein said support structure is attached at one end thereof to a circumferential portion of said opaque, semi-cylindrical, substantially cradle member such that said support structure can be wrapped around a circumference of said cradle member.

8. The non-invasive electro-optical sensor according to claim 1 wherein said support structure is attached at one end thereof to an end portion of said opaque, semi-cylindrical, substantially cradle member such that said support structure can be wrapped around an axis of said cradle member.

9. The non-invasive electro-optical sensor according to claim 1 wherein said adhesive layer comprises a separate double-sided adhesive layer applied to said concave surface of said cradle member.

10. A non-invasive electro-optical sensor for removable adhesive attachment to a fingertip of a patient for use in measuring light extinction during transillumination of the blood-perfused tissue within said fingertip, said sensor comprising:

an opaque, semi-cylindrical, substantially rigid cradle member having a concave surface, a convex surface and a diameter larger than the diameter of a human fingertip;

a flexible, initially substantially planar web-like support structure attached at one end thereof to said cradle member;

a light source mounted on said concave surface of said cradle member;

a photosensor mounted in said web like support structure, said photosensor having a photo-sensitive surface which directly overlies said light source when said support structure is wrapped around a human fingertip within said cradle member; and an adhesive layer on said concave surface of said cradle member for removably adhesively securing said concave surface of said cradle member to a fleshy portion of a human fingertip such that said concave surface is held in conformance with said human fingertip without stressing said human fingertip.

11. The non-invasive electro-optical sensor according to claim 10 further including means for securing said support structure in a wrapped position around a human fingertip within said cradle member such that said light source directly overlies said photosensor.

12. The non-invasive electro-optical sensor according to claim 10 wherein said opaque, semi-cylindrical, substantially rigid cradle member is constructed of molded polyolefin plastic.

13. The non-invasive electro-optical sensor according to claim 12 wherein said opaque, semi-cylindrical, substantially rigid cradle member is constructed of polypropylene.

14. The non-invasive electro-optical sensor according to claim 10 further including a recess within said concave surface of said cradle member for receiving said light source.

15. The non-invasive electro-optical sensor according to claim 10 further including an electrical conductor channel formed within said concave surface of said cradle member.

16. The non-invasive electro-optical sensor according to claim 10 wherein said support structure is attached at one end thereof to a circumferential portion of said opaque, semi-cylindrical, substantially cradle member such that said support structure can be wrapped around a circumference of said cradle member.

17. The non-invasive electro-optical sensor according to claim 10 wherein said support structure is attached at one end thereof to an end portion of said opaque, semi-cylindrical, substantially cradle member such that said support structure can be wrapped around an axis of said cradle member.

18. The non-invasive electro-optical sensor according to claim 10 wherein said adhesive layer comprises a separate double-sided adhesive layer applied to said concave surface of said cradle member.

* * * * *

UNITED STATES PATENT AND TRADEMARK OFFICE
CERTIFICATE OF CORRECTION

PATENT NO. : 5,891,021
DATED : April 6, 1999
INVENTOR(S) : Andrew Joseph Dillon, et al.

It is certified that error appears in the above-identified patent and that said Letters Patent is hereby corrected as shown below:

On the title page item [75] "Todd Johnson" should read -- Todd Johnson Daniel --.

Signed and Sealed this

Thirty-first Day of August, 1999

Attest:

Q. TODD DICKINSON

*Attesting Officer*    *Acting Commissioner of Patents and Trademarks*